(12) United States Patent
Takeda et al.

(10) Patent No.: US 8,491,853 B2
(45) Date of Patent: Jul. 23, 2013

(54) SUBSTRATE AND DEVICE FOR BIOASSAY AND METHOD FOR MAKING THE SUBSTRATE

(75) Inventors: Minoru Takeda, Tokyo (JP); Motohiro Furuki, Tokyo (JP); Tatsumi Ito, Tokyo (JP)

(73) Assignee: Sony Corporation, Tokyo (JP)

( * ) Notice: Subject to any disclaimer, the term of this patent is extended or adjusted under 35 U.S.C. 154(b) by 902 days.

(21) Appl. No.: 11/435,822

(22) Filed: May 18, 2006

(65) Prior Publication Data

US 2006/0275181 A1 Dec. 7, 2006

(30) Foreign Application Priority Data

May 19, 2005 (JP) .................. 2005-146607

(51) Int. Cl.
| | |
|---|---|
| *B01L 3/00* | (2006.01) |
| *C12Q 1/00* | (2006.01) |
| *C12Q 1/34* | (2006.01) |
| *B01D 57/02* | (2006.01) |
| *B01D 59/42* | (2006.01) |
| *B01D 59/50* | (2006.01) |
| *B01D 61/42* | (2006.01) |

(52) U.S. Cl.
USPC ............. 422/503; 436/514; 435/4; 435/18; 204/450

(58) Field of Classification Search
USPC ....................................... 422/102
See application file for complete search history.

(56) References Cited

U.S. PATENT DOCUMENTS

| 6,773,566 B2* | 8/2004 | Shenderov ............... 204/450 |
|---|---|---|
| 2003/0219713 A1* | 11/2003 | Valencia et al. ............ 435/4 |
| 2005/0014286 A1* | 1/2005 | Furuki et al. ............ 436/514 |
| 2005/0048595 A1* | 3/2005 | Yamatsu et al. ........... 435/18 |
| 2005/0112548 A1* | 5/2005 | Segawa et al. ............ 435/4 |
| 2006/0128030 A1 | 6/2006 | Mamine et al. |
| 2006/0166216 A1 | 7/2006 | Nakao et al. |

FOREIGN PATENT DOCUMENTS

| CN | 133015 A | 1/2002 |
|---|---|---|
| CN | 1455002 A | 11/2003 |
| DE | 102 53 077 A1 | 5/2004 |
| EP | 0 417 305 | 3/1991 |
| EP | 1 491 875 | 12/2004 |
| EP | 1 520 623 | 4/2005 |
| EP | 1 520 623 A2 | 4/2005 |

(Continued)

OTHER PUBLICATIONS

First Office Action for Application No. 2006100806047, the State Intellectual Property Office of the People's Republic of China, mailed Jun. 19, 2009.

(Continued)

*Primary Examiner* — Sam P Siefke
*Assistant Examiner* — Bryan Kilpatrick
(74) *Attorney, Agent, or Firm* — Finnegan, Henderson, Farabow, Garrett & Dunner, LLP

(57) ABSTRACT

A substrate for bioassay comprises a substrate and a group of reaction regions serving as a field where interaction between substances proceeds and formed in the substrate, and a group of information pits used to obtain positional information of individual reaction regions and/or substance information used in the reaction regions. The group of reaction regions and the group of information pits are not formed in the same substrate surface. A bioassay apparatus using the substrate and a method for making the substrate are also provided.

10 Claims, 6 Drawing Sheets

FOREIGN PATENT DOCUMENTS

| | | |
|---|---|---|
| EP | 1 637 872 A1 | 3/2006 |
| EP | 1 643 250 A1 | 4/2006 |
| JP | 11-076765 | 3/1999 |
| JP | 2001-238674 | 9/2001 |
| JP | 2002-014106 | 1/2002 |
| JP | 2002-250726 | 9/2002 |
| JP | 2004-93548 | 3/2004 |
| JP | 2004-135512 | 5/2004 |
| JP | 2004-257962 | 9/2004 |
| JP | 2005-3450 | 1/2005 |
| JP | 2005-003450 | 1/2005 |
| JP | 2005-506530 | 3/2005 |
| WO | WO 2004/089546 | 10/2004 |
| WO | WO 2004/089546 A2 | 10/2004 |
| WO | WO 2004/111620 | 12/2004 |
| WO | WO 2004/111620 A1 | 12/2004 |
| WO | WO 2005/003770 A1 | 1/2005 |

OTHER PUBLICATIONS

Office Communication from the European Patent Office in Application No. 06252486.3, dated Jun. 18, 2012.

* cited by examiner

SUBSTRATE AND DEVICE FOR BIOASSAY AND METHOD FOR MAKING THE SUBSTRATE

CROSS REFERENCES TO RELATED APPLICATIONS

The present invention contains subject matter related to Japanese Patent Application JP2005-146607 filed with the Japanese Patent Office on May 19, 2005, the entire contents of which being incorporated herein by reference.

BACKGROUND OF THE INVENTION

This invention relates to a technique related to a substrate for bioassay. More particularly, the invention relates to a substrate and device suited for bioassay for measuring and detecting interaction between substances and also to a method for making the substrate.

At present, substrates that are called a DNA chip or DNA microarray (hereinafter referred generically to DNA chip) wherein a given DNA is (in full length or partly) microsequenced have been utilized for mutation evolution, SNP's (single nucleotide polymorphisms) analysis, a frequency analysis of genomic expression and the like and are now being used widely in other fields of drug discovery, clinical diagnosis, pharmacogenomics, forensic medicine and the like.

In the DNA chip, it is general to fix a nucleic acid strand called probe against a surface site of a reaction field provided on a substrate and detect hybridization between the probe nucleic acid strand waiting for at the reaction field and a fluorescence-labeled target nucleic acid strand by measuring an intensity of target nucleic acid-derived fluorescence.

Alternatively, a method of detecting hybridization has been proposed, in which an intercalator capable of emitting fluorescence through specific binding to a complementary strand produced by hybridization is used for measuring an intensity of fluorescence from the intercalator.

Still alternatively, there has also been proposed a technique wherein a counter electrode is provided at a reaction field on a DNA chip and an electric field is applied thereto, with which it is intended to improve a hybridization efficiency and detection accuracy by the electrodynamic action (see Japanese Laid-open Patent Application No. 2004-135512 as Patent Document 1).

In recent years, there have been proposed DNA chips, to which an information reading technique of optical disks such as CD, DVD and the like or an optical disk mastering technique is applied. For instance, Patent Document 2 (Japanese Laid-open Patent Application No. 2005-3450) discloses a DNA chip wherein a reaction region (corresponding to a data region) serving as a field of hybridization and address pits for obtaining positional information of the reaction region and rotational synchronism information on the same plane of a disk-shaped substrate (see FIG. 1 of Patent Document 2).

Patent Document 3 (Japanese Laid-open Patent Application No. 2004-93548) proposes a disk-shaped medium wherein microcapillaries capable of isolating a sample component by electrophoresis are formed.

SUMMARY OF THE INVENTION

If both reaction regions corresponding to data regions of an optical disk and a group of information pits providing positional information of the reaction regions and substance information are formed on the same plane or surface of a substrate, there arises a technical problem in that since a solvent is stored in the reaction regions of the substrate for bioassay, a tracking servo following the information pit group is susceptible to receive a disturbance owing to the presence of the reaction regions.

Further, the presence of the reaction regions makes it unstable to read the positional information and substance information of the information pit group. In particular, a technical problem is involved in that with a substrate arrangement wherein an electrode layer (conductive layer) is formed on the surface where the information pit group has been formed, reading of information from the information pit group becomes more instabilized.

Accordingly, in the invention, it is a aim to provide a substrate for bioassay that enables an optical pickup means of the type similar to that of an optical disk reproducing apparatus to obtain information related to the interaction between substances from reaction regions on a substrate and also to more stably obtain information from an information pit group formed on the substrate.

The invention contemplates to provide a substrate for bioassay, which comprises a group of reaction regions serving as a field where interaction between substances proceeds and a group of information pits used to obtain positional information of the respective region regions and/or substance information used in the reaction regions wherein the substrate is so arranged that the group of reaction regions and the group of information pits are not formed on the same substrate surface. The arrangement where the group of reaction regions and the group of information pits are not formed on the same substrate surface should not be construed as limited narrowly. In a preferred instance, the group of reaction regions are formed on one substrate surface and the group of information pits are formed on or in the other surface, with which it is designed not to form the group of reaction regions and the group of information pits on or in the same substrate surface.

Alternatively, a substrate is provided in which a group of reaction regions are formed at an upper surface side and a group of information pits are formed at a lower surface side, under which an optically transparent substrate capable of transmitting light of a given wavelength (e.g. fluorescence exciting light, tracking servo light, focusing servo light or the like) may be disposed on the lower surface side. In this case, an optical pickup operation can be performed from the lower surface side of the substrate.

Further, a conductive layer acting as an electrode may be formed on the substrate surface where the group of reaction regions have been formed. Since no group of information pits are formed on this substrate surface, reading of the group of information pits suffers no influence of the conductive layer, thus being stabilized. It will be noted that the use of the conductive layer as an electrode for application of an electric field is optional. For instance, opposed electrodes are formed using the conductive layer and a conductive cover substrate covering the group of reaction regions, under which an electric field may be applied to individual reaction regions via the opposed electrodes. The cover substrate may be formed with holes, through which a sample solution is introduced into individual reaction regions.

The shape of the substrate for bioassay according to the invention is not critical and preferably includes a form of disk. With this form, an optical pickup means as used in optical disks such as CD, CVD and the like may be adopted.

Individual reaction regions of the reaction region group disposed at the substrate surface allow a probe substance waiting for a target substance, which serves as a counterpart of an interaction such as hybridization, to exist in a free or fixed state. According to fluorescence information obtained from a fluorescent substance labeled to the probe substance or target substance, the interaction can be detected. Alternatively, according to fluorescence information obtained from a fluorescent substance specifically bound to a product obtained through the interaction between the probe substance and the target substance, the interaction can be detected.

Next, the invention provides a bioassay device which comprises a fluorescence detection unit for detecting a fluorescence intensity by irradiating fluorescence exciting light against a group of reaction regions provided at a substrate for bioassay so as to obtain a fluorescence serving as occurrence information of interaction, under which the fluorescence is focused, and a servo unit for obtaining positional information of the respective reaction regions of the reaction region group and/or substance information employed in the respective reaction regions by irradiating a laser beam of a given wavelength against the group of information pits to perform focusing servo and tracking servo.

In this bioassay device, the measurement of fluorescence after the interaction in the reaction regions can be effected by use of an optical pickup as used in existing optical disk reproducing apparatuses to obtain data of a detected fluorescence intensity related with the positional information of the respective reaction regions and substance-related information such as of a probe substance.

Moreover, the invention provides a method for making a substrate for bioassay, which is characterized by comprising subjecting a synthetic resin material to injection molding to provide a substrate that is provided with a group of reaction regions serving as a field where the interaction between substances proceeds and a group of information pits used to obtain positional information of the reaction regions and/or substance information used within the reaction regions in such a way that the group of reaction region are formed on one surface and the group of the information pits are formed on the other surface and both surfaces are simultaneously, integrally molded. The simultaneous integral molding of both sides ensures positional registration between the group of reaction regions and the group of information pits in high accuracy.

The main technical terms related to the invention are defined or illustrated hereinbelow.

The term "interaction" is intended to widely mean noncovalent bond, covalent bond, chemical bond including hydrogen bond or dissociation between substances and, for example, mean hybridization between nucleic acid molecules, interaction between proteins, chemical bond between substances in antigen-antibody reaction or dissociation. It will be noted that the term "hybridization" means a reaction for forming a complementary strand (a double strand) between complementary base sequence structures.

The term "probe substance" means a substance that is present in a solvent stored or kept in a reaction region and functions as a probe (detector) for detecting a substance (target substance) to specifically interact with the probe substance and is allowed to exist in the reaction regions in a free state or exist as fixed at one end thereof to a solid phase surface.

The term "target substance" is a substance provided for a sample for the purpose of checking whether a specific interaction with the above-defined probe substance is carried out.

The term "nucleic acid strand" means a polymer (a nucleotide strand) of nucleoside phosphate wherein purine or a pyrimidine base and sugar are subjected to glucoside bond and widely covers DNA's (in full length or fragments thereof) that are polymers of oligonucleotides including probe DNA, polynucleotide or purine nucleotide and pyrimidine nucleotide, cDNA obtained by reverse transcript, RNA, polyamide nucleotide derivatives (PNA) and the like.

The term "reaction region" is a region capable providing a field of interaction such as hybridization and one instance includes a reaction field having a well form capable of storing a liquid phase or gel therein.

The term "information pit" is a site formed in a substrate surface and capable of being utilized for obtaining positional information of reaction regions, information related to a substance existing in a reaction region, and information of tacking or focusing. Pit arrays for information can be in conformity with the format, for example, of CD (compact disk) or DVD (digital versatile disk).

The term "substrate for bioassay" means a substrate that allows interaction between substances in given reaction regions of the substrate to proceed so as to detect the interaction and encompasses a wide variety of substrates irrespective of the types of substances without objection to the detection principle of the interaction. The substrate for bioassay includes, at least, a DNA chip (a DNA microarray) wherein a nucleic acid strand such as a DNA probe is fixed in a microsequence and a protein chip suited to detect an interaction between proteins or an antigen-antibody reaction.

According to the invention, the substrate is so arranged that the group of reaction regions and the group of information pits are not formed on the same substrate surface, so that data information, related to the interaction between substances, from the reaction regions on the substrate can be obtained by an optical pickup means of the type as used in optical disk reproducing apparatuses and simultaneously, information from the group of information pits formed on the substrate can be more stably obtained.

DETAILED DESCRIPTION OF THE PREFERRED EMBODIMENTS

Preferred embodiments of the invention are illustrated with reference to the accompanying drawings. It will be noted that the embodiments shown in the accompanying drawings are instances of typical embodiments of a substrate, an apparatus and a method according to the invention, which should not be construed as limiting the invention thereto.

Figure 1:
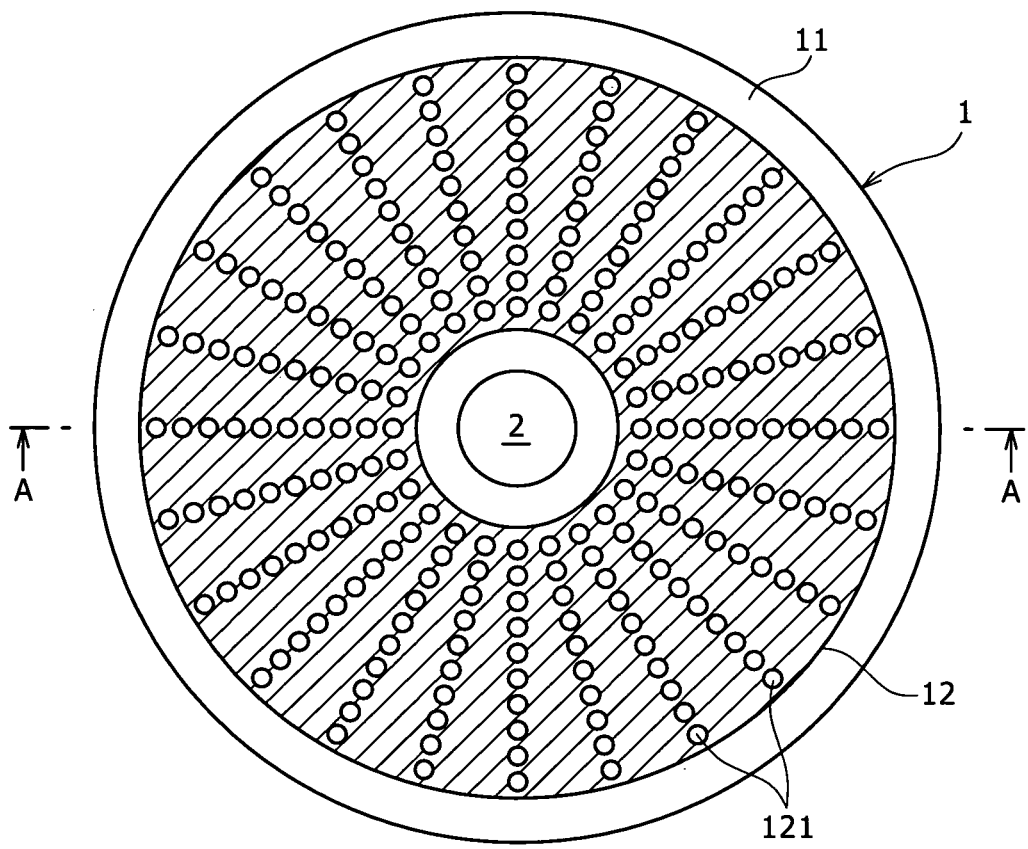
FIG. 1 is a plan view, as seen from above, of a substrate for bioassay according to an embodiment of the invention.

FIG. 1 is a plan view, as viewed from above, of a substrate for bioassay according to one embodiment of the invention. In FIG. 1, a substrate for bioassay indicated at 1 is one which is used to detect interaction between substances. The substrate is made of a disk-shaped plate similar to optical disks such as CD (compact disk), DVD (digital versatile disk) and the like. It is to be noted that although the substrate for bioassay of the invention is not limited to a disk-shaped form in a narrow sense, it is as a matter of fact that if it has a disk shape, apparatuses and techniques used for existing optical disks can be conveniently employed.

At the center of the substrate 1 for bioassay, a central hole 2 is formed. When the substrate 1 is mounted on a given type of analyzer, a chucking mechanism for holding and rotating the substrate 1 is inserted into the central hole 2.

The substrate 1 for bioassay is broadly constituted of a lower side multi-layered substrate 11 and a cover substrate 12 having an outer diameter smaller than the lower substrate 11. The cover substrate 12 has a multitude of holes 121, which correspond, in number, to reaction regions 3 (not shown in FIG. 1), radially arrayed as viewed from above (see FIG. 1). It will be noted that the cover substrate 12 is utilized as an electrode in this embodiment and is formed of a conductive material.

Figure 2:
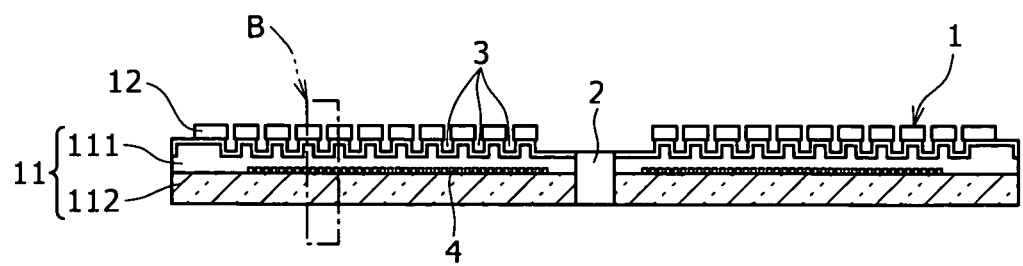
FIG. 2 is a section view of the substrate, taken along line A-A of FIG. 1.
Figure 3:
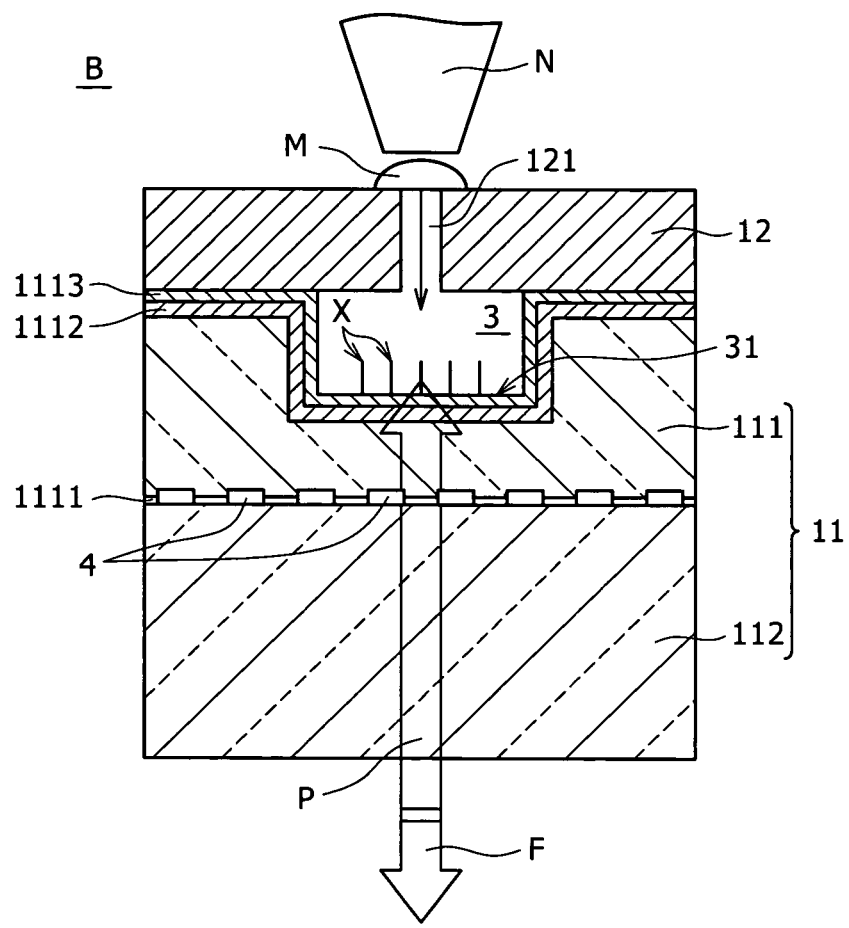
FIG. 3 is an enlarged, sectional view of part B of FIG. 2.

FIG. 2 is a sectional view of the substrate as viewed along the direction of arrows A-A, and FIG. 3 is an enlarged sectional view of a portion B in FIG. 2. Referring to FIGS. 2 and 3, the lower side multi-layered substrate 11 is formed with a multitude of wells serving as reaction regions 3,3 . . . at the upper surface side thereof and is provided, at the lower surface side thereof, with an optically transparent, first substrate 111 having a multitude of information pits 4,4 . . . formed in arrays. Moreover, the first substrate 111 is provided with an optically transparent, second substrate 112 at the lower side thereof.

A reflection film 1111 (see FIG. 3) having a specified reflectance is formed on the surface of the first substrate 111 where the information pits 4 are formed. This reflection film 1111 is bonded to the upper surface of the second substrate 112. The reflection film 1111 serves to selectively reflect tracking servo light or the like irradiated toward the information pits 4.

On the other hand, a necessary number of micro-wells are formed at the upper surface side of the first substrate 111, and the well functions as a reaction region 3 that is a field of interaction between substances. This well is so designed as to have a depth and a size (e.g. a diameter of 500 µm and a dept of 5 µm) sufficient to permit a liquid, such as a sample solution, to be kept therein when such a liquid is dropped.

Figure 4:
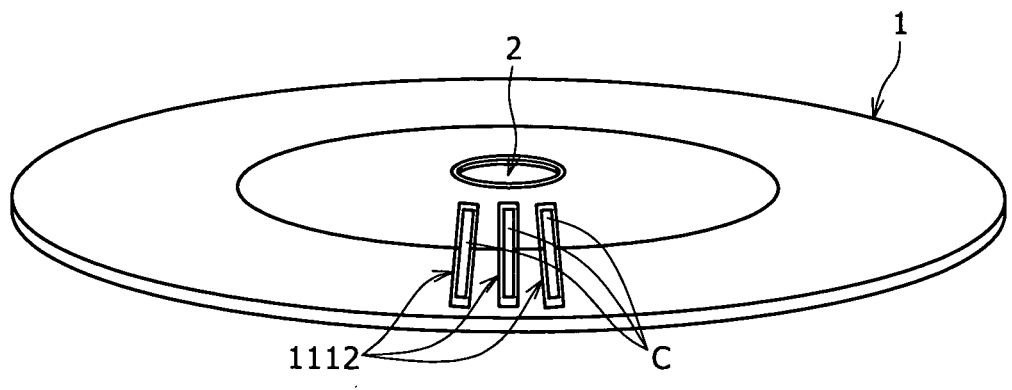
FIG. 4 is a view showing a substrate for bioassay (in a cover substrate-free state) disposed with channels (C) functioned as reaction regions.
Figure 5:
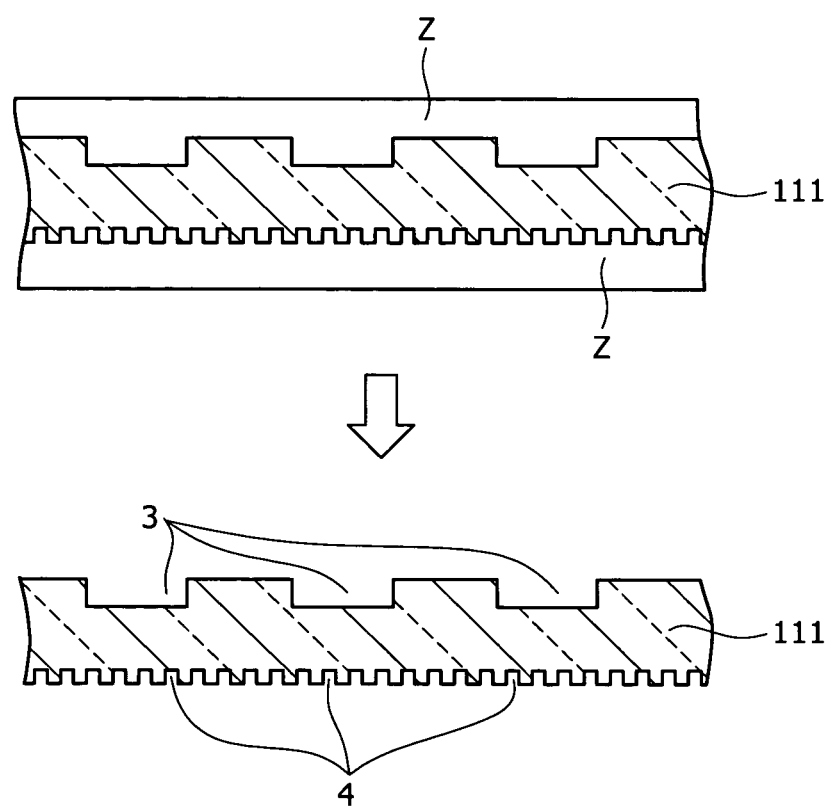
FIG. 5 is a schematic view showing the concept of injection molding of a first substrate (111)

The reaction regions 3 on the first substrate 111 may be in a mutually independent well form as shown in FIG. 2. Alternatively, the regions may be formed as channels C extended radially from the center and disposed at given intervals along a peripheral direction (se FIG. 4).

As shown in FIG. 3, the first substrate 111 is formed, on the upper surface thereof, with a transparent electrode layer 1112 made of ITO (indium tin oxide) or the like in a thickness, for example, of about 150 nm. A solid phase layer 1113 suited to fix a probe substance X is further stacked on the transparent electrode layer 1112.

The solid phase layer 1113 is formed of a material suited to fix the probe substance X at one terminal of the molecule thereof. For instance, $SiO_2$ capable of surface modification with a silane compound is formed as a film in a thickness of about 50 nm. The solid phase layer 1113 formed such as of $SiO_2$ functions as an insulating layer and thus, can prevent occurrence of an electrochemical reaction with an ionic solution that may be stored in the reaction region 3, in some case.

The solid phase layer 1113 is exposed to a bottom 21 (see FIG. 3) of the reaction region 3, and the exposed surface portion is surface-treated, for example, with a silane coupling agent. The probe substance X can be chemically joined at a modified terminal functional group thereof with a free amino group of the silane coupling agent. That is, the probe substance can be fixed. Alternatively, the probe X may be fixed by use of a diazo coupling reaction.

The first substrate 111 and second substrate 112 are, respectively, formed of a material or materials permitting transmission of fluorescence exciting light P exciting a fluorescent material in the reaction region 3 and fluorescence F that is generated by excitation with the fluorescence exciting light P (see FIG. 3). For instance, the first substrate 111 and the second substrate 112 are favorably constituted of a material or materials such as an optically transparent synthetic resin, glass or the like, respectively. If the information pits 4 are in a CD format, the second substrate is set at a thickness of 1.2 mm. Likewise, if the information pits 4 are in a DVD format, the second substrate is set at a thickness of 0.6 mm.

The first substrate 111 is so arranged as to separately form a group of reaction regions 3 and a group of information pits 4 at the front surface (upper surface) and back surface (lower surface) thereof, respectively. The substrate 111 of this arrangement is conveniently manufactured by injection molding of a thermoplastic resin according to a simultaneous, double-sides molding process using stampers (molds) Z, Z separately engraved with individual patterns of the reaction regions 3 and the information pits 4. The reason for this is that the molding is completed in one step and is thus simple and positional registration of the reaction regions 3 and the information pits 4 can be performed in high accuracy.

Next, the cover substrate 12 can be made up entirely of a metallic substrate or sheet (see FIG. 3). Instead, a synthetic resin substrate or sheet which is formed at part thereof with an electrode layer such as an ITO film or the like may be used for this purpose (not shown). This cover substrate 12 may be bonded to the first substrate 111 after having been positionally registered, or may be mounted to the first substrate 111 in the course of application of an electric field to the reaction regions 3 or when interaction is allowed to proceed, whichever may be selected depending on the purpose.

As indicated hereinbefore, the cover substrate 12 is formed, at the center thereof, with the hole 121, through which a sample solution M is introduced into the reaction region 3. The hole 121 is so formed as having a size (or a diameter) that is smaller than an opening of the reaction region 3 and is sufficient to have the sample solution M introduced into the well in high accuracy. It will be noted that symbol N shown in FIG. 3 indicates a nozzle for dropping the sample solution M toward the hole 121.

A sample solution containing several types of probe substances X is introduced into an intended reaction region 3 or a group of reaction regions from the nozzle N through the hole 121 of the cover substrate 12, and the respective probe substances X are fixed to the bottoms 31 of individual reaction regions 3. Subsequently, according to an introduction procedure as with the probe substance X, a sample solution containing a target substance Y labeled with a fluorescent substance f is introduced into the respective reaction regions 3 to permit interaction between the substances X and Y to proceed.

Figure 6:
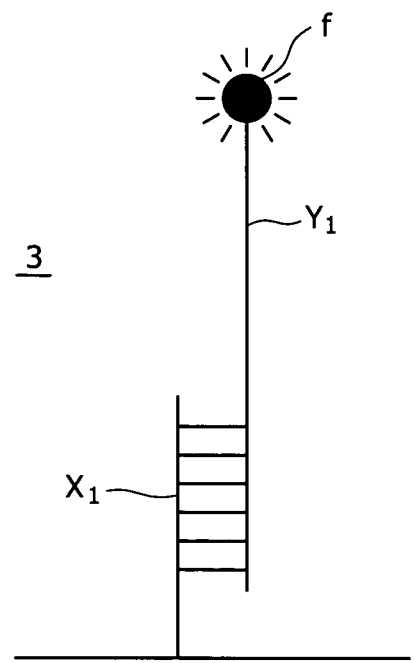
FIG. 6 is a schematic view illustrating an embodiment of detecting hybridization by measuring fluorescence from a fluorescence-labeled target nucleic acid strand ($Y_1$)

In FIG. 6, there is schematically shown how a probe nucleic acid strand $X_1$ and a fluorescence-labeled target nucleic acid strand $Y_1$ are hybridized (an instance of interaction) in the reaction region 3 to form a complementary strand (double strand). In this case, the fluorescence information from the target nucleic acid strand $Y_1$ becomes information showing occurrence of hybridization. More particularly, an intense fluorescence can be measured in the reaction region wherein there exist the target nucleic acid strand $Y_1$ and the probe nucleic acid strand $X_1$ having a complementary base sequence.

Figure 7:
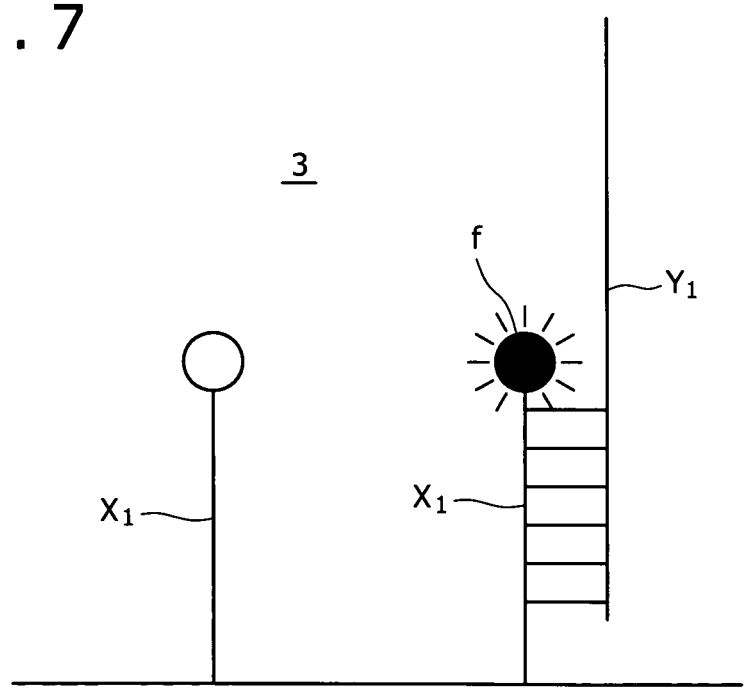
FIG. 7 is a schematic view illustrating an embodiment of detecting hybridization by measuring fluorescence from a fluorescence-labeled probe nucleic acid strand ($X_1$)

The hybridization may be detected by labeling the probe nucleic acid strand $X_1$ with the fluorescent substance f and measuring the resulting fluorescence. For instance, as shown in FIG. 7, the probe nucleic acid strand $X_1$ may be labeled with the fluorescent substance f in such a way that fluorescence is emitted only when hybridization proceeds, under which fluorescence from an intercalator I is measured to detect hybridization.

Figure 8:
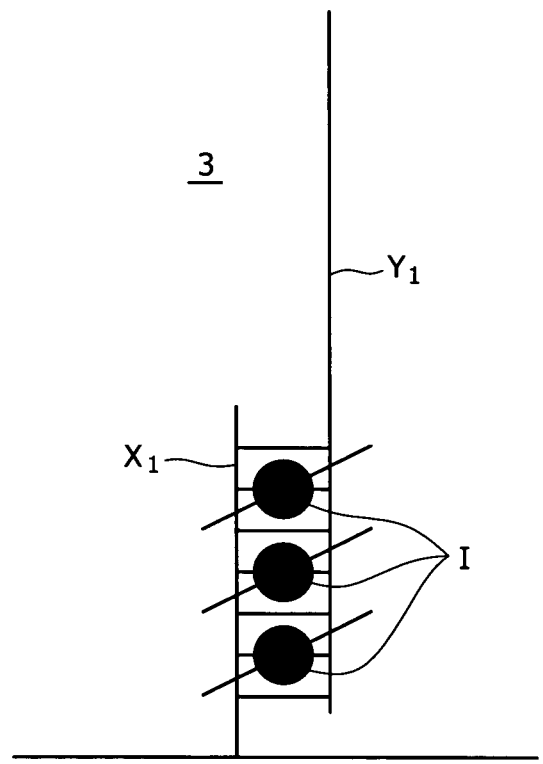
FIG. 8 is a schematic view illustrating an embodiment of detecting hybridization by measuring fluorescence from an intercalator (I) specifically bound to a complementary strand.

Alternatively, as shown in FIG. 8, hybridization may be detected by introducing a fluorescent intercalator I, which is specifically bound to a complementary strand portion, into the reaction region 3 and measuring fluorescence from the intercalator. The introduction timing of the intercalator I is not critical. For example, the intercalator may be introduced simultaneously with the target nucleic acid strand $Y_1$ or may be introduced after progress of hybridization.

The substrate 1 for bioassay is so arranged as to have the transparent electrode layer stacked on the first substrate 111 and the cover substrate 12 serving as a counter electrode, so that an electric filed can be applied to the reaction region 3 via the counter electrode. For instance, in case of detecting hybridization or the like, hybridization may be allowed to proceed under conditions where a high frequency AC voltage of 5V and 1 MHz is applied, thereby applying an electric field of about 1 V/μm to the reaction regions 3.

For the electrodynamic action of application of an electric field on the interaction between substances, mention is made of electrophoresis, dielectrophoresis and the like. These electrodyanamic action may be appropriately selected depending on the type of interaction and the purpose, thereby achieving an improved probability of association between substances and dissolution of a steric trouble upon the interaction. Hence, the efficiency of interaction can be enhanced and high-speed assay operations can be attained, thereby enabling one to increase a detection accuracy of interaction.

Although not specifically shown in the drawings, an uneven electric field can be more effectively established in the vicinity of the transparent electrode layer 1112 when the transparent electrode layer 111 is partly formed at the bottom of the reaction region 3 or at part of the bottom than when the transparent layer 1112 is provided wholly over the first substrate 111. In the latter case, the electrophoretic action can be effectively utilized. Such a partial transparent electrode layer 1112 can be made using a metal mask having openings at portions corresponding to the reaction regions 3, for example, when ITO is sputtered on the first substrate 111 in the form of a film.

As stated hereinbefore, the substrate 1 for bioassay has the information pits 4 capable of reading by irradiating a laser beam for CD or DVD from the lower side thereof. Using the information pits 4, the positional information (address information) of individual reaction regions 3 of the substrate 1 can be optically read, thereby making it possible to identify which reaction region of the group of reaction regions 3 is subjected to fluorescence detection operations.

Especially, with the substrate 1 for bioassay being in a disk form, if a reproduction system as used in an optical disk system is used, there can be detected a focusing servo control for controlling a focusing position of a laser beam, a positioning servo control for controlling an irradiation position of a laser beam along a radial direction and a dropping position of a dropping device such as the nozzle N, and the information pits 4. In other words, when an information content recorded as the information pits 4 and the reaction regions 3 located just thereon are designed to correspond to each other, a laser beam can be irradiated only against a specified reaction region 3 to effect a fluorescence detection operation.

Figure 9:
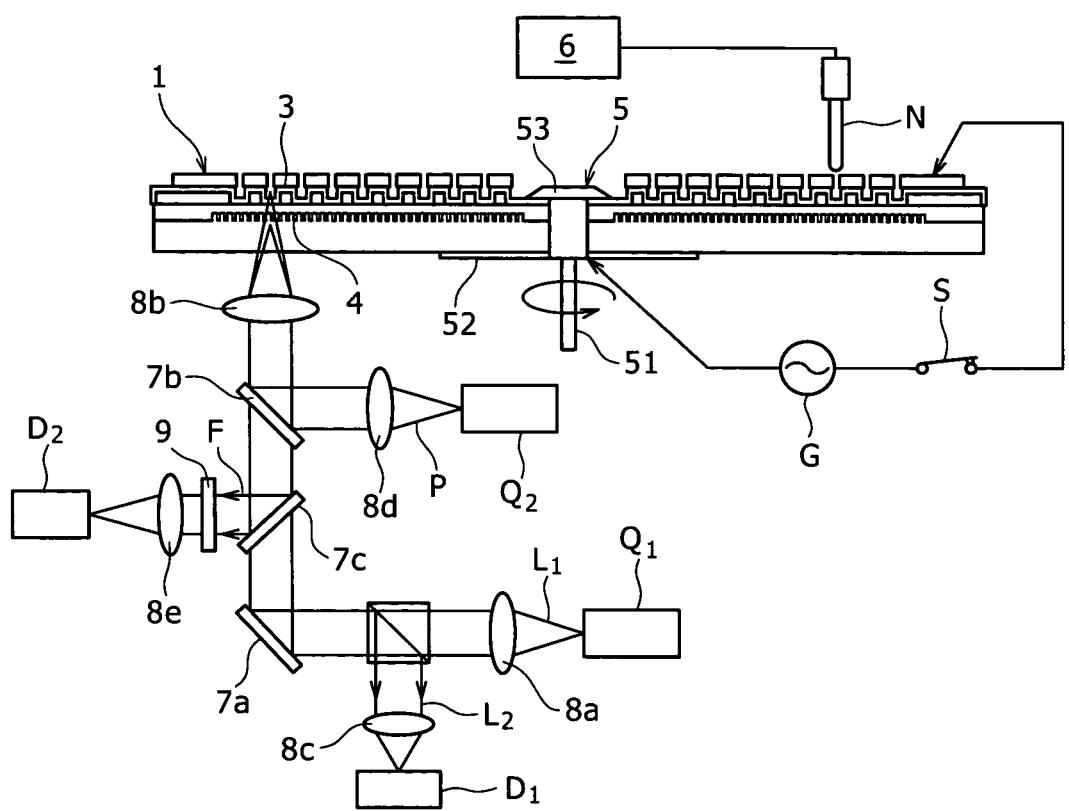
FIG. 9 is a schematic view showing a bioassay apparatus according to an embodiment of the invention.

One instance of an interaction detection procedure using the substrate 1 for bioassay having such an arrangement as set out hereinabove is illustrated. FIG. 9 is a view showing an embodiment of a bioassay apparatus suitable for carrying out the procedure.

It will be noted that the case where interaction is hybridization is described hereinbelow and, particularly, an instance of the case where this hybridization is detected by use of intercalator I (see FIG. 8) is specifically set out.

Initially, the substrate 1 for bioassay is held and rotated by a chucking mechanism 5, like an optical disk drive, as shown in FIG. 1. This chucking mechanism 5 is connected to a rotary drive shaft and has a central shaft 51, a turn plate 52 that is formed vertically to the center shaft and supports the substrate 1 for bioassay from the lower surface side, and a chucking claw 53 holding the substrate 1 from the upper surface side (see FIG. 9). The turn plate 52 and the chucking claw 53 are, respectively, attached to the central shaft 51 and rotated along with the central shaft 51.

When the chucking mechanism 5 is inserted into the center hole 2 of the substrate 1 for bioassay, an electrode of the chucking mechanism 5 and a contact portion of the substrate are brought into contact with each other to allow electric conduction.

Subsequently, a sample solution containing a probe DNA modified with a specific type of functional group (e.g. an amino group or a carboxyl group) at one end thereof is fed to the dropping nozzle N from a reservoir 6 disposed above the substrate and dropped into a given reaction region 3 through the nozzle N.

Upon the feed, the substrate 1 for bioassay is so rotated that the probe DNA is dropped into individual reaction regions while controlling the relative position between the specified reaction region 3 and the dropping nozzle N. According to such a dropping operation as mentioned above, several types of probe DNA's are, respectively, dropped in predetermined reaction regions 3 of the substrate 1 provided that one type of probe DNA has to be fed into one reaction region 3.

Whether which types of probe DNA's are dropped in the respective region regions is determined by preparing beforehand an arrangement map showing the relationship between the reaction regions 3 and the probe DNA's and controlling the dropping based on the arrangement map. Under conditions where give types of DNA solutions are, respectively, filled in all the reaction regions 3, the substrate 1 for bioassay is held in position to cause the probe DNA to the bottom of individual reaction regions 3.

Likewise, a sample solution containing a target DNA and a fluorescent intercalator I (see FIG. 7) is dropped in the respective reaction regions, under which an electric field (e.g. a high frequency AC electric field of about 1 MV/m and 1 MHz) is applied between the upper and lower electrodes, i.e. between the transparent electrode layer 1112 and the cover electrode 12, through an outer power source G (see FIG. 9). Symbol S in FIG. 9 indicates a switch for on-off operation on application of an electric field.

When such an electric filed is applied to, the target DNA floating in the solution in the reaction region is moved (migrated), by the electrodynamic action such as dielectrophoresis, toward the bottom 31 of the reaction region 3 where the probe DNA has been fixed, thereby permitting concentration of the target DNA to increase around the probe DNA. Consequently, when the target DNA and the probe DNA are such that mutual base sequences are in a complementary relation, hybridization is caused to occur in an efficient manner. At the time, the intercalator I is bound to a complementary strand or strands of the probe DNA and the target DNA where hybridization has occurred.

Subsequently, like the drive system of optical disks, the substrate 1 for bioassay is controlled in drive to detect fluorescence from the reaction region 3. More particularly, as shown in FIG. 9, the substrate 1 is rotated while holding and, at the same time, a laser beam $L_1$ of a given wavelength is outputted from a laser beam source $Q_1$ and passed through a forward lens 8*a*. After change of a direction of the beam passage or progress with a mirror 7*a*, the beam is irradiated and focused to the information pit 4 via a les 8*b* (capable of driving with an actuator, not shown) located at a lower side of the substrate 1 for bioassay. Scattered reflection light $L_2$ from the information pit 4 is passed through the mirror 7*a* and the lens 8*c* and detected with a photodetector (PDIC) $D_1$ to specify a position of the reaction region 3.

Simultaneously, fluorescence exciting light P is outputted from a laser beam source $Q_2$ such as, for example, a blue semiconductor laser (Blue-LD) and passed through a forward mirror 8*d* for conversion to parallel beams, after which the beam-progressing direction is changed with the mirror 7*b* (dychroic mirror), followed by focusing with the lens 8*b* disposed at the lower side of the substrate 1 and irradiating toward the reaction region 3.

Fluorescence F generated by excitation in the reaction region 3 is fed out from the lower surface side of the substrate 1 and separated with the mirror 7*b*, followed by changing a beam-progressing direction with a subsequent mirror 7*c*, passing through a filter 9 and a lens 8*e* and detecting with a photodetector (PMT) $D_2$. The resulting fluorescence is compared with optical information from the information pit 4 to determine which reaction region 3 takes part in the generation of fluorescence.

Subsequently, there is made a map showing positions of the reaction regions 3 generating fluorescence among the group of the reaction regions 3 on the substrate for bioassay. The thus made map is compared with a probe arrangement map indicating a probe DNA of which base sequence is dropped to which of the reaction regions 3, thereby analyzing the base sequence of the target DNA.

As stated hereinbefore, the substrate 1 for bioassay according to the invention is so arranged that the reaction regions 3 and the information pits 4 are separately formed on different surfaces of the substrate according to a method such as a simultaneous, double-sided method. Hence, when a fluorescence intensity is detected after hybridization by focusing and irradiating a laser bema $Q_1$ for CD or DVD at the surface side of the substrate where the information pits are formed, the positional information and the like of the reaction regions 3 can be accurately read out without suffering a disturbance with the reaction regions storing the sample solution M therein and the electrode layer (transparent electrode layer 1112). At the same time, a laser beam $Q_2$ for fluorescence excitation is irradiated and focused at the reaction region 3, a fluorescence intensity can be detected in high accuracy.

The present invention can be utilized in the field of bioassay techniques for detecting interaction substances. For instance, the invention can be used as a technique related to sensor chips, typical of which is a DNA chip.

It should therefore be understood by those skilled in the art that various modifications, combinations, sub-combinations and alterations may occur depending on design requirements and other factor in so far as they are within the scope of the appended claims or the equivalents thereof.

What is claimed is:

1. A substrate for bioassay, comprising:
    a first substrate having a group of reaction regions formed on an upper surface thereof and a group of information pits formed on a lower surface thereof, the group of information pits being used to obtain positional information of individual reaction regions and/or substance information used in the reaction regions, and the group of reaction regions and the group of information pits lying in a same optical path;
    a second substrate abutting the lower surface of the first substrate;
    a reflection film formed on the lower surface of the first substrate where the group of information pits are formed and bonded to an upper surface of the second substrate;
    a transparent electrode layer formed on the upper surface of the first substrate; and
    a conductive cover substrate disposed over the first substrate, the cover substrate including a plurality of holes corresponding in number to the reaction regions, and having an outer diameter smaller than the first substrate, wherein the conductive cover substrate is a counter electrode configured to apply an electric field to at least one of the group of reaction regions.

2. The substrate according to claim 1, wherein the information pits are located at positions on the lower surface corresponding to the reaction regions, respectively.

3. The substrate according to claim 1, wherein the second substrate is optically transparent.

4. The substrate according to claim 1, wherein sample solutions are introduced through the plurality of holes in the cover substrate into the respective reaction regions.

5. The substrate according to claim 1, wherein the substrate has a disk form.

6. The substrate according to claim 1, wherein a probe substance to interact with a target substance is present in a free or fixed state in the respective reaction regions.

7. The substrate according to claim 6, wherein the interaction is detected by fluorescence information obtained from a fluorescent substance labeled to the probe substance or the target substance.

8. The substrate according to claim 6, wherein the interaction is detected by fluorescence information obtained from a fluorescence substance specifically bound to a product that is obtained by interaction between the probe substance and the target substance.

9. The substrate according to claim 6, wherein the interaction is hybridization between the probe substance acting as a complementary nucleic acid strand and the target substance.

10. A bioassay apparatus comprising:
    a fluorescence detecting unit for detecting a fluorescence intensity by irradiating fluorescence exciting light against a group of reaction region provided in the substrate for bioassay defined in claim 1 so as to obtain fluorescence serving as occurrence information of interaction, under which the exciting light is focused; and
    a servo unit for obtaining positional information of individual reaction regions of the group and/or substance information used in individual reaction regions by irradiating a laser beam of a given wavelength against the group of information pits and performing a focusing servo and a tracking servo.

* * * * *